United States Patent [19]

Panek

[11] Patent Number: 5,362,473

[45] Date of Patent: Nov. 8, 1994

[54] RADIOLABELLED PARTICULATE COMPOSITION

[75] Inventor: Karel J. Panek, Heiloo, Netherlands

[73] Assignee: Mallinckrodt Medical, Inc., St. Louis, Mo.

[21] Appl. No.: 678,252

[22] PCT Filed: Oct. 6, 1989

[86] PCT No.: PCT/US89/04490

§ 371 Date: Dec. 18, 1991

§ 102(e) Date: Dec. 18, 1991

[30] Foreign Application Priority Data

Oct. 14, 1988 [NL] Netherlands .................. 8802530

[51] Int. Cl.$^5$ .............................................. A61K 49/02
[52] U.S. Cl. .................................................. 424/1.13
[58] Field of Search ................ 424/1.1, 9, 1.13, 1.25; 514/770, 957, 958, 959

[56] References Cited

U.S. PATENT DOCUMENTS

| | | | |
|---|---|---|---|
| 4,042,677 | 8/1977 | Molinski et al. | 424/1 |
| 4,280,991 | 7/1981 | Burch | 424/1 |
| 4,643,891 | 2/1987 | Panek | 424/1.1 |
| 4,671,958 | 6/1987 | Rodwell et al. | 424/85 |
| 4,707,352 | 11/1987 | Stavrianpoulos | 424/1.1 |
| 4,871,716 | 10/1989 | Longo et al. | 514/2 |
| 5,130,118 | 7/1992 | Johnson et al. | 424/1.1 |

OTHER PUBLICATIONS

Namenyi et al., "Radiolabelled Pulmonary Diagnostic Agent," *Hung. Teljes,* HU45199 A2, 28 Jun. 1988 (CA110(7):53864f).

*Primary Examiner*—Robert L. Stoll
*Assistant Examiner*—Lara E. Chapman

[57] ABSTRACT

The invention relates to a metal-radionuclide-labelled particulate composition which may be used in the form of a dry aerosol for lung scintigraphy, in particular, for the examination of the mucociliary transport, or for radiotherapy. The composition comprises radioactive labelled particles on a base of silica gel, another silicaceous material or a non-swelling polymer, at the surface of which organic ligands are bound covalently which comprise thiol-, amino-, alkylamino-, oxime-, dithiocarbamate-, xanthate-, thiosemicarbazone-, or dithiosemicarbazone groups or combinations thereof.

The invention further relates to a method of preparing the composition and to a kit for carrying out the method.

9 Claims, No Drawings

RADIOLABELLED PARTICULATE COMPOSITION

The present invention relates to a metal-radionuclide-labelled particulate composition which may be used in the form of a dry aerosol for lung scintigraphy or for radiotherapy of diseases of the respiratory system, to a method of preparing the composition and to a kit for carrying out the method. The invention further relates to a method of performing a radiodiagnostic lung examination, in particular of the mucociliary transport systems.

Radiolabelled aerosols have been used for lung scintigraphy for some 15 years already, usually for lung ventilation studies and to detect and localize lung abnormalities. It is desirable for this purpose to cause deposition of aerosol particles to take place in the alveoli, hence alveolarly. A nebulizer developed for this purpose which generates aerosol particles having an average diameter of 0.8 $\mu$m, is described by Kotrappa c.s. in J. Nucl. Med. 18 1977, 1082–1085. An improved aerosol generator-inhalator with which dry aerosol particles having a smaller spreading in particle size can be generated is the subject of European Patent Application 85200830.9.

The present invention relates in particular to a radiolabelled particulate composition which after nebulization may be used for the examination of the mucociliary transport system and hence of bronchial diseases which are related to an unsatisfactory functioning of the mucociliary transport system. In the non-respiratory part of the bronchial tubes there exists a very effective barrier against inhaled particles which may comprise toxic or infectious agents and may have allergenic or carcinogenic effects. This barrier is formed by a mucus layer which is transported in the direction of the mouth in a constant stream by microscopically small cilia. This transport is termed the mucociliary transport. Conditions for an undisturbed mucociliary transport are a normal coordinated cilia movement and a normal mucus production. An unsatisfactory functioning of the mucociliary transport may play a part in chronic bronchial diseases. A simple and reliable method of measuring the mucociliary transport is therefore of extremely great importance. In fact, a considerable part of the world population suffers from bronchial diseases and for these CARA-patients a good method of diagnosis is indispensable before medical treatment can proceed. However, good quantitative methods to measure the mucociliary transport have failed so far. In the past a number of invasive or semi-invasive methods were used which, in addition to the disadvantage of the medical surgery as such, also influence the mucociliary transport itself unfavorably, so that the results obtained are not reliable.

It is the object of the present invention to provide a radiolabelled particulate composition which after nebulization may be used for lung scintigraphy and which is intended in particular for the examination of the mucociliary transport. The particles of the composition, to be suitable for the examination of the mucociliary transport, must satisfy various requirements:

(1) During the transport through the lungs the dimensions of the particles should not vary; this means that the particles should not become smaller due to evaporation, but also that they should not grow, for example, as a result of active absorption of water by the particles.

(2) After nebulization the aerosol particles must have a small spreading in particle size to enable a selective examination.

(3) The particles should permit easy radiolabelling and the radioactive "label" should be sufficiently stable, i.e. should not be released from the particles during the nebulization, breathing and the subsequent lung examination.

(4) The particles must have a suitable aerodynamic shape; preferably spherical, to be able to reach the lung tissue to be examined.

(5) The basic material of the particles should be sufficiently stable to enable the desired lung examination and should be completely inert with respect to the lung tissue, i.e. it should be so tolerable for the lungs that even the mucociliary transport is not influenced by it.

This object can be achieved by means of a particulate composition which is labelled with a metal-radionuclide and which according to the present invention is characterized in that it comprises radiolabelled particles having a base of silica gel, another siliceous material or a non-swelling polymer, at the surface of which organic ligands are bonded covalently, the ligands comprising thiol-, amino-, alkylamino-, oxime-, dithiocarbamate-, xanthate-, thiosemicarbazone- or dithiosemicarbazone groups or combinations thereof. In addition to silica gel, other siliceous materials may be used as a base material, for example, glass, aluminum silicate or other silicates. Suitable non-swelling polymers are highly cross-linked polymeric compounds selected from polystyrene, divinyl benzene polycarbonates, polyamides and polyfluoralkanes. Silica gel, porous glass or other porous silicates are the preferred base materials. These base materials are available in the aerodynamic shape and size suitable for the inventive purpose and in the desired small spreading in particle size desired for the intended use. Furthermore, these materials have been found to be sufficiently stable and entirely inert with respect to the lung tissue. However, it is difficult to find materials which in addition satisfy the above-mentioned requirement (3): permitting easy radiolabelling and after labelling being sufficiently stable for the intended use. Unfortunately, all types of particulate materials which are readily available and would in principle be suitable for the desired application, cannot be used as such because they cannot be labelled or can hardly be labelled with the desired radionuclides.

It has been found that the above-mentioned particulate materials can simply be treated at their surfaces in such a manner that after the treatment they can easily be labelled with a metal-radionuclide. In silica particles or in particles of another siliceous material the surface treatment can be carried out in a simple manner by treating the particles with organic compounds which comprise thiol-, amino-, alkylamino-, oxime-, dithiocarbamate-, xanthate-thiosemicarbazone- or dithiosemicarbazone groups. Examples of suitable agents for this purpose are alkoxy silanes which comprise such groups, for example, mercaptopropyl trimethoxysilane, N-(2-aminoethyl-3-aminopropyl) trimethoxysilane and the like. Optionally, these particles provided with primary groups, for example, thiol-, amino-, alkylamino or oxime groups, may be converted in a further treatment into particles which comprise at their surfaces ligands with dithiocarbamate-, xanthate-, thiosemicarbazoneor dithiosemicarbazone groups. Surface treatment of polymeric materials may in principle be carried out in two manners namely (1) by a pre-treatment of the monomer of oligomer, followed by a (further) polymerization or a cross-linking, or (2) by a treatment of the already cross-linked polymer. According to the last-mentioned method a polymer comprising benzene rings may be treated, for example, with acetic acid anhydride under Friedel-Crafts conditions, after which the introduced acetyl groups may be converted in a subsequent reaction into ligands with thiol-, amino-, etc. -groups. A suitable starting polymer for this latter method is, for example, a highly cross-linked macroporous non-swelling poly(divinylbenzene) resin in which the benzene rings can easily be acetylated. The introduced acetyl groups can simply be converted into other functional groups, for example, in a successive oxidation and double esterification in which a polymeric resin is obtained which is ligandated with hexylthioglycolate groups, i.e. in which the benzene rings comprise $CO_2(CH_2)_6OCOCH_2SH$-groups.

When the composition according to the invention is intended for examination of the mucociliary transport, deposition of the aerosol particles in the alveoli should be avoided as much as possible. Alveolar activity causes radioactivity to spread too much, resulting in less reliable information and an undesirable radiation burden on the alveoli. Therefore, it is necessary to impose stringent requirements on the particle size and spreading in particle size of the inhaled aerosol particles. It has been found that particles having an average diameter from 1 to 20 μm, preferably from 2 to 10 μm, are most suitable for examining the mucociliary transport because the particles can then selectively reach the upper bronchi but cannot penetrate to the alveoli.

Metal-radionuclides suitable for labelling the particulate composition which is destined for lung scintigraphy are Tc-99m, Pb-203, Ga-67, Ga-68, As-72, In-111, In-113m and Ru-97. Technetium-99m is preferred because of its radiation characteristics and availability.

A particulate composition according to the invention, provided it comprises a suitable radiation source, may also be used therapeutically, namely for diseases of the respiratory system which can be reached by such a particulate composition. The following radionuclides are suitable for therapeutically active compositions: Re-186, Re-188, Cu-67, Pb-212, Bi-212, As-77, Y-90, Ag-111 and Pd-109.

The invention further relates to a method of preparing a composition by a complex-forming reaction of a salt or a chelate of a metal-radionuclide with a particulate material on a base of silica gel or another siliceous material, the particles being modified at their surfaces as described hereinbefore. Suitable chelators for the metal-radionuclide will be mentioned hereinafter.

Because of the often short half-life of the metal-radionuclide, it is often impossible to place the ready-for-use labelled composition at the user's disposal. In such cases the user will perform the labelling reaction with the radionuclide in the clinic or the clinical laboratory. Therefore, the various reaction components are supplied to the user in a kit. The operations to be performed by the user should be as simple as possible, without need for laborious separation or purification, to enable the user to prepare the radioactive-labelled composition by means of the auxiliary means available from the supplied kit. The labelling efficiency or labelling yield also plays an important part.

The present invention also relates to a kit, comprising (1) a particulate material as defined hereinbefore, which may be in a dry condition, optionally to which one or more auxiliary substances, e.g. stabilizers and dispersing agents, have been added, (2) a solution of a salt or a chelate of a metal-radionuclide, and optionally (3) instructions for use comprising a prescription for reacting (1) with (2). Examples of suitable stabilizers are ascorbic acid, gentisic acid or salts of these acids; examples of suitable dispersing agents are: non-ionic surface-active substances, e.g. polyoxyalkyl compounds and the like. Furthermore, other auxiliary substances may be added, for example, fillers, e.g. glucose, lactose, mannitol, inositol, and the like.

In the labelling reaction the metal-radionuclide is preferably presented to the particulate material in the form of a chelate. In order to produce the desired complex-forming reaction the radionuclide is preferably bonded to comparatively weak chelators, for example, a pyrophosphate, a phosphonate, a polyphosphonate, an oxinate, a carboxylate, a hydroxycarboxylate, an aminiocarboxylate, an enolate or a mixture thereof. Examples of suitable chelators for the radionuclide are 8-hydroxyquinolin polycarboxylic acids or hydroxycarboxylic acids, such as oxalic acid, malonic acid, succinic acid, maleic acid, orthophthalic acid, malic acid, lactic acid, tartaric acid, citric acid, ascorbic acid, salicylic acid or derivatives of these acids; pyrophosphates or polyphosphonates, such as methylene diphosphonate, hydroxyethylene diphosphonate or hydroxymethylene diphosphonate; or enolates, for example, with a β-diketone, such as acetylacetone, furoylacetone, thenoyl-acetone, benzoylacetone, dibenzoyl methane, tropolone, or derivatives of these diketones. In particular, 8-hydroxyquinolin, citric acid, tartaric acid, ascorbic aid, glucoheptonic acid or a derivative thereof, or acetylacetone are preferred as chelators, because it has been found that a chelate of a radionuclide, for example, indium-111 or lead-203, with one of these chelators in a suitable medium, preferably a buffered aqueous solution, easily reacts at a physiological pH with a surface modified particulate material, the desired radionuclide complex being formed in a high yield and purity by ligand exchange. The supplied kit may also consist of the constituent (1) optionally, with instructions for use, whereas, the solution of the metal-radionuclide, (2) having a limited shelf life, may be supplied separately to the user.

To prepare a technetium-99m-labelled particulate composition in a preferred embodiment of the present invention, the kit may comprise (1) a particulate material as defined hereinbefore which may be in a dry condition, optionally, to which one or more auxiliary substances, e.g. stabilizers and dispersing agents, have been added, and optionally (2) instructions for use with a prescription for reacting (1) with a solution of reduced technetium-99m in the form of a salt of a chelate. The solution of reduced technetium-99m in the form of a salt or a chelate may be supplied to the user separately or may simply be prepared by the user by obtaining a pertechnetate solution from a molybdenum-technetium generator available to the user and reducing the solution, optionally in the presence of a chelator. As a chelator for Tc-99m one of the chelators mentioned hereinbefore may be used. A similar kit may be used for the preparation of an Re-188-labelled radiotherapeutic composition, with adapted instructions for use.

In another preferred embodiment, the kit for preparing a technetium-99m-labelled composition comprises the following ingredients: (1) a particulate material as defined hereinbefore, which may be in a dry condition, optionally to which one or more auxiliary substances, e.g. stabilizers and dispersing agents, have been added; (2) a chelator as described hereinbefore and a reducing agent; and optionally (3) instructions for use with a prescription for reacting ingredients (1) and (2) with technetium-99m in the form of a pertechnetate solution or with rhenium-188 in the form of a perrhenate solution. The composition should include a reducing agent to reduce the pertechnetate or perrhenate. The above ingredients (1) and (2) may optionally be combined, provided they are compatible. Such a mono-component kit in which the combined ingredients are preferably lyophilized, is exceptionally suitable to be reacted with the radionuclide solution in a simple manner by the user.

For the pertechnetate or perrhenate it is preferred to use a reducing agent which does not influence the labelling reaction, for example, a dithionite, formamidine sulfinic acid, diaminemethane disulfinate or complexes of suitable reducing metals, such as Sn(II), Cu(I), Fe(II), etc. The constituent (1) of the kits may be supplied as a suspension but is preferably present in a dry condition, for example, in a lyophilized condition.

The present invention further relates to a method of performing a radiodiagnostic lung examination, in particular of the mucociliary transport system, the method comprising nebulizing a radioactive-labelled particulate composition, for example by means of the aerosol generator described in European Patent Application 85200830.9 now European Patent Number 166,476; allowing a warm-blooded living being, in particular a human being, to inhale the resulting dry aerosol in a quantity from 1 to 2,000 MBq, preferably from 50 to 1,000 MBq, per 70 kg of body weight; and recording the radiation emitted by the being, for example, by means of a gamma camera.

The present invention also relates to a method of subjecting a warm-blooded living being to a radiotherapeutic treatment, especially for treating certain diseases of the respiratory system, the method comprising nebulizing a particulate composition labelled by a radionuclide suitable for this purpose, and allowing the living being to inhale the resulting dry aerosol in a quantity which is effective for controlling lung tumors.

The invention will now be described in greater detail with reference to specific examples.

EXAMPLE I

Preparation of silica gel particles with terminal thiol groups

Approximately 5 ml of 1N hydrochloric acid are added to approximately 100 ml of a 10% v/v solution of mercaptopropyltrimethoxysilane in acetonitrile. The resulting reaction mixture, after homogenization, is immediately poured on approximately 50 g of dry, acid-prewashed silica gel particles, (Bakerbond® 100, 5 μm) thereby forming a slurry. The reaction is allowed to proceed at room temperature for 10 minutes under slow stirring. The slurry is then filtered through a glass filter and washed with three portions (50-75 ml) of acetonitrile, after which the resulting product is dried overnight at room temperature under a vacuum. The resulting particulate product is analyzed for the content of free SH-groups, using a iodometric titration. The results show that the product comprises approximately 14±1 mg of SH per gram.

In the same manner, silica gel particles having a diameter of 10 μm (LiChrospher® Si 100, 10 μm) are provided with terminal thiol groups.

In a corresponding manner, chemically bound $NH_2$ groups containing ligands are bound to the surface of the silica gel particles by treating the silica gel particles with a 10% solution of N-(2-aminoethyl-3-aminopropyl) trimethoxysilane in 0.1% aqueous acetic acid.

EXAMPLE II

The radioactive labelling of the modified silica gel particles with technetium-99m as Tc-99m glucoheptonate A solution of Tc-99m glucoheptonate is obtained by adding 10 ml of a solution of Tc-99m pertechnetate in a physiological saline solution (from a molybdenum-technetium generator) to a commercially available glucoheptonate kit, comprising calcium gluheptonate and tin(II)chloride (reducing agent) in a lyophilized condition. The incubation time is 15 minutes; radioactivity 0.7-1.1 GBq.

The radioactive labelling of the silica gel particles modified with terminal thiol groups and obtained according to Example I is carried out as follows. 1.0 ml of the above Tc-99m glucopheptonate solution (70-110 MBq) is added to 5 mg of the modified silica gel particles. After incubation on a boiling-water bath (T=approximately 100° C.) for approximately 15 minutes, the reaction mixture is filtered through a G4 glass filter and washed with physiological saline solution. From measurement of the radioactivity it appears that the labelling is complete: greater than 98%. The same labelling efficiency can be achieved at room temperature; with careful stirring of the reaction mixture, for example, by means of a magnetic stirrer. The 5 μm and 10 μm modified silica gel particles may be labelled in the same manner.

EXAMPLE III

The radioactive labelling of the modified silica gel particles with technetium-99m as sodium pertechnetate in the presence of a reducing agent The silica gel particles of 5 μm and 10 μm modified with terminal thiol groups and obtained according to Example I are treated directly with Tc-99m pertechnetate from a Mo-Tc generator in the presence of sodium dithionite as a reducing agent. The labelling is carried out under nitrogen in otherwise the same reaction condition as described in Example II; the labelling efficiency is greater than 96%.

The resulting radioactive-labelled compositions may be nebulized to a dry aerosol and, after inhaling by a patient, may be used for lung scintigraphic examination.

EXAMPLE IV

Preparation of silica gel particles with terminal dithiocarbamate groups

A suspension is made of 15 g of the silica gel particles modified with terminal amino groups and obtained according to Example I in 75 ml of water. 19.0 ml of 1N sodium hydroxide solution, 19.0 ml of isopropanol and 15 ml of carbon disulfide are added successively while stirring. The reaction mixture is stirred at room temperature for 15 minutes and then filtered through a fine sintered-glass filter. The wet filter cake is washed three times with 75 ml of isopropanol and dried in vacuo at room temperature. The dry silica gel modified with dithiocarbamate groups is stored in the refrigerator under nitrogen.

The concentration of the free dithiocarbamate groups is determined by iodometric titration and by determination of the sorption capacity for Cu(II). It appears from both methods that the concentration of dithiocarbamate groups is approximately 0.9–0.5 mmol/g of dry material.

Silica gel modified with terminal xanthate groups is prepared in a corresponding manner. As a starting material are used pure unmodified silica gel particles which are treated successively with benzene, isopropanol, carbon disulfide and a methanolic solution of tetramethyl ammonium hydroxide.

EXAMPLE V

The radioactive labelling of the silica gel particles modified with dithiocarbamate groups using technetium-99m as Tc-99m glucoheptonate Approximately in the same manner as described in Example II, but this time with careful stirring at room temperature, silica gel particles having diameters of 5 μm and 10 μm and modified as described in Example IV are labelled. A radiometric determination demonstrates that the labelling takes place with an efficiency of greater than 96%.

EXAMPLE VI

Stability of silica gel particles labelled with Tc-99m

The stability of silica gel particles labelled with Tc-99m in various media is determined as follows:

Selection incubation media:
(1) 0.9% NaCl solution in water;
(2) 0.09% NaCl solution in water;
(3) distilled water;
(4) 50% solution of ethanol in water; and
(5) an inactive solution of glucoheptonate kit as described in Example II, dissolved in 10 ml of physiological saline solution.

The following experiments are carried out for each of the above-mentioned incubation media. A set of 21 tubes each comprising 25 mg of silica gel particles, modified with terminal thiol groups according to Example I, is labelled by means of Tc-99m glucoheptonate as described in Example II. The labelled silica gel particles are then separated by filtration, washed with 1 ml of the selected incubation medium and resuspended in 1 ml of the same medium. These samples are left to stand at room temperature for 3.5 hours (incubation time), during which period they are carefully stirred from time to time. Each set of samples is analyzed in triplicate with time intervals of 15–30 minutes; the labelling percentage, i.e. the Tc-99m activity still bound to the silica gel after the above incubation time, is determined. The average labelling percentages are recorded in the following table.

It appears from the results in the following table that Tc-99m is firmly bound to the labelled silica gel particles and has not reached or has hardly reached one of the examined incubation media during the incubation time of 3.5 hours. This time is approximately the maximum time which is to be expected for a diagnostic examination. No difference in stability is found for 5 μm and 10 μm silica gel particles.

TABLE

| time min. | labelling percentage in incubation medium: | | | | |
|---|---|---|---|---|---|
| | (1) | (2) | (3) | (4) | (5) |
| 15 | 98.10 ± 0.04 | — | 98.37 ± 0.71 | 97.97 ± 0.79 | 98.77 ± 0.18 |
| 30 | 98.63 ± 0.08 | — | 98.45 ± 1.51 | — | — |
| 45 | 98.44 ± 0.12 | 96.57 ± 0.55 | — | 98.70 ± 1.24 | 98.17 ± 0.31 |
| 60 | — | 95.90 ± 1.38 | — | — | — |
| 75 | — | — | — | 98.13 ± 1.72 | 98.33 ± 0.47 |
| 90 | — | 98.17 ± 1.79 | 94.93 ± 2.59 | — | — |
| 105 | 98.17 ± 0.24 | — | — | — | — |
| 120 | 97.15 ± 0.46 | 96.45 ± 2.12 | 97.42 ± 3.75 | 98.48 ± 2.14 | 98.22 ± 0.95 |
| 150 | 97.66 ± 0.65 | 94.43 ± 3.30 | 98.64 ± 3.79 | 98.56 ± 2.69 | — |
| 180 | 97.06 ± 0.92 | — | 98.86 ± 4.07 | 99.04 ± 2.95 | 99.27 ± 1.14 |
| 210 | — | 95.88 ± 3.54 | — | — | — |

What is claimed is:

1. A technetium-99m-labelled particulate composition to be used as a dry aerosol for lung scintigraphy, the composition comprising technetium-99m-labelled particulate base material wherein said base material is selected from the group consisting of a silica gel, a siliceous material, and a non-swelling polymer; wherein organic ligands are bonded covalently to the surface of the base material, the organic ligands including at least one functional moiety selected from the group consisting of thiol-, amino-, alkylamino-, oxime-, dithiocarbamate-, xanthate-, thiosemicarbazone-, or dithiosemicarbazone groups or combinations thereof, said technetium-99m-labelled particulate composition forming a dry aerosol.

2. A composition according to claim 1, wherein the base material is a non-swelling highly cross-linked polymer selected from the group consisting of polystyrene, divinylbenzene, polycarbonates, polyamides, and fluoroalkyl polymers.

3. A composition according to claim 1, wherein the base material is selected from the group consisting of a silica gel, a porous glass, and a porous silicate.

4. A composition according to claim 1, wherein the technetium-99m-labelled particles have an average diameter from 1 μm to 20 μm.

5. A composition according to claim 4, wherein the technetium-99m-labelled particles have an average diameter from 2 μm to 10 μm.

6. A method of preparing a technetium-99m-labelled particulate composition to be used as a dry aerosol for lung scintigraphy, the composition comprising technetium-99m-labelled particulate base material wherein said base material is selected from the group consisting of a silica gel, a siliceous material, and a non-swelling polymer; wherein organic ligands are bonded covalently to the surface of the base material, the organic ligands including at least one functional moiety selected from the group consisting of thiol-, amino-, alkylamino-, oxime-, dithiocarbamate-, xanthate-, thiosemicarbazone-, or dithiosemicarbazone groups or combinations thereof; the method comprising: reacting technetium-99m with said base material having said organic ligands covalently bonded to the surface of the base material so as to form a technetium-99m chelate complex with said organic ligands, wherein said reacting step occurs in an aqueous medium so as to form a technetium-99m-labelled particulate composition; and nebulizing said technetium-99m-labelled particulate composition to form a dry aerosol.

7. A method for performing a radiodiagnostic lung examination, comprising:
(a) nebulizing a technetium-99m-labelled particulate composition, the composition comprising technetium-99m-labelled particles on a base material selected from the group consisting of a silica gel, a siliceous material, and a non-swelling polymer; wherein organic ligands are bonded covalently at the surface of the base material, the organic ligands including at least one functional moiety selected from the group consisting of thiol-, amino-, alkylamino-, oxime-, dithiocarbamate-, xanthate-, thiosemicarbazone-, or dithiosemicarbazone groups or combinations thereof; to form a dry aerosol;
(b) administering said dry aerosol by inhalation to a warm-blooded living being in a quantity from 1 to 2,000 MBq, per 70 kg of body weight; and
(3) recording radioactive radiation emitted by said living being.

8. A method according to claim 7, wherein the examination is of the mucociliary transport system.

9. A method according to claim 7, wherein the dry aerosol is inhaled in a quantity of 50–1,000 MBq, per 70 kg of body weight.

* * * * *